(12) United States Patent
Sandberg et al.

(10) Patent No.: US 6,506,731 B1
(45) Date of Patent: Jan. 14, 2003

(54) ELASTIN PEPTIDE ANALOGS AND METHODS OF USING SAME

(75) Inventors: Lawrence B. Sandberg, Colton, CA (US); Thomas F. Mitts, Visalia, CA (US)

(73) Assignee: Connective Tissue Imagineering LLC, Visalia, CA (US)

(*) Notice: Subject to any disclaimer, the term of this patent is extended or adjusted under 35 U.S.C. 154(b) by 30 days.

(21) Appl. No.: 09/584,001

(22) Filed: May 30, 2000

Related U.S. Application Data

(63) Continuation-in-part of application No. 09/039,308, filed on Mar. 13, 1998, now Pat. No. 6,069,129, and a continuation-in-part of application No. PCT/US99/05496, filed on Mar. 12, 1999.

(51) Int. Cl.$^7$ .......................... A61K 38/08; A61K 38/12
(52) U.S. Cl. .................... 514/15; 514/8; 514/9; 514/16; 530/304; 530/317; 530/327; 530/328; 530/329
(58) Field of Search .................. 514/16, 15, 9, 514/6; 530/304, 317, 327, 328, 329

(56) References Cited

U.S. PATENT DOCUMENTS 5,945,409 A  *  8/1999  Crandall ...................... 514/78

* cited by examiner

*Primary Examiner*—Michael Borin
(74) *Attorney, Agent, or Firm*—Benesch, Friedlander, Coplan & Aronoff LLP

(57) ABSTRACT

The present invention is directed to a composition which is used to enhance the elasticity and/or appearance of tissue. Specifically, the present invention is directed to a composition formulated from peptides having low molecular weights and which substantially correspond to sequences found in elastin More preferably, the present invention corresponds to the general formula $R_1$-Leucine-Glycine-Alanine-Glycine-Glycine-Alanine-Glycine-$R_2$.

16 Claims, 4 Drawing Sheets

SEQUENCE LISTING

<160> NUMBER OF SEQ ID NOS: 75

<210> SEQ ID NO 1
<211> LENGTH: 3
<212> TYPE: PRT
<213> ORGANISM: mammalian

<400> SEQUENCE: 1

Ala Val Gly
 1

<210> SEQ ID NO 2
<211> LENGTH: 4
<212> TYPE: PRT
<213> ORGANISM: mammalian

<400> SEQUENCE: 2

Val Gly Ala Gly
 1

<210> SEQ ID NO 3
<211> LENGTH: 3
<212> TYPE: PRT
<213> ORGANISM: mammalian

<400> SEQUENCE: 3

Ile Gly Gly
 1

<210> SEQ ID NO 4
<211> LENGTH: 2
<212> TYPE: PRT
<213> ORGANISM: mammalian

<400> SEQUENCE: 4

Leu Gly
 1

<210> SEQ ID NO 5
<211> LENGTH: 4
<212> TYPE: PRT
<213> ORGANISM: mammalian

<400> SEQUENCE: 5

Ile Gly Ala Gly
 1

<210> SEQ ID NO 6
<211> LENGTH: 3
<212> TYPE: PRT
<213> ORGANISM: mammalian

<400> SEQUENCE: 6

Leu Gly Gly
 1

<210> SEQ ID NO 7
<211> LENGTH: 4
<212> TYPE: PRT
<213> ORGANISM: mammalian

<400> SEQUENCE: 7

Val Ala Pro Gly

```
<210> SEQ ID NO 8
<211> LENGTH: 4
<212> TYPE: PRT
<213> ORGANISM: mammalian

<400> SEQUENCE: 8

Leu Gly Pro Gly
  1

<210> SEQ ID NO 9
<211> LENGTH: 4
<212> TYPE: PRT
<213> ORGANISM: mammalian

<400> SEQUENCE: 9

Leu Gly Ala Gly
  1

<210> SEQ ID NO 10
<211> LENGTH: 4
<212> TYPE: PRT
<213> ORGANISM: mammalian

<400> SEQUENCE: 10

Val Gly Pro Gly
  1

<210> SEQ ID NO 11
<211> LENGTH: 4
<212> TYPE: PRT
<213> ORGANISM: mammalian

<400> SEQUENCE: 11

Phe Gly Pro Gly
  1

<210> SEQ ID NO 12
<211> LENGTH: 4
<212> TYPE: PRT
<213> ORGANISM: mammalian

<400> SEQUENCE: 12

Val Gly Pro Gln
  1

<210> SEQ ID NO 13
<211> LENGTH: 3
<212> TYPE: PRT
<213> ORGANISM: mammalian

<400> SEQUENCE: 13

Leu Gly Ala
  1

<210> SEQ ID NO 14
<211> LENGTH: 4
<212> TYPE: PRT
<213> ORGANISM: mammalian

<400> SEQUENCE: 14

Val Gly Pro Ala
  1
```

```
<210> SEQ ID NO 15
<211> LENGTH: 4
<212> TYPE: PRT
<213> ORGANISM: mammalian

<400> SEQUENCE: 15

Val Val Pro Gly
 1

<210> SEQ ID NO 16
<211> LENGTH: 4
<212> TYPE: PRT
<213> ORGANISM: mammalian

<400> SEQUENCE: 16

Ala Val Pro Gly
 1

<210> SEQ ID NO 17
<211> LENGTH: 4
<212> TYPE: PRT
<213> ORGANISM: mammalian

<400> SEQUENCE: 17

Val Val Pro Gln
 1

<210> SEQ ID NO 18
<211> LENGTH: 6
<212> TYPE: PRT
<213> ORGANISM: mammalian

<400> SEQUENCE: 18

Val Ala Ala Arg Pro Gly
 1               5

<210> SEQ ID NO 19
<211> LENGTH: 7
<212> TYPE: PRT
<213> ORGANISM: mammalian

<400> SEQUENCE: 19

Leu Gly Ala Gly Gly Ala Gly
 1               5

<210> SEQ ID NO 20
<211> LENGTH: 4
<212> TYPE: PRT
<213> ORGANISM: mammalian

<400> SEQUENCE: 20

Ala Ile Pro Gly
 1

<210> SEQ ID NO 21
<211> LENGTH: 5
<212> TYPE: PRT
<213> ORGANISM: mammalian

<400> SEQUENCE: 21

Leu Gly Pro Gly Gly
 1               5

<210> SEQ ID NO 22
```

```
<211> LENGTH: 5
<212> TYPE: PRT
<213> ORGANISM: mammalian

<400> SEQUENCE: 22

Ala Ala Ala Gln Ala
 1               5

<210> SEQ ID NO 23
<211> LENGTH: 5
<212> TYPE: PRT
<213> ORGANISM: mammalian
<220> FEATURE:
<223> OTHER INFORMATION: Xaa, position 4, is hydroxyproline

<400> SEQUENCE: 23

Val Gly Val Xaa Gly
 1               5

<210> SEQ ID NO 24
<211> LENGTH: 5
<212> TYPE: PRT
<213> ORGANISM: mammalian

<400> SEQUENCE: 24

Val Tyr Pro Gly Gly
 1               5

<210> SEQ ID NO 25
<211> LENGTH: 6
<212> TYPE: PRT
<213> ORGANISM: mammalian

<400> SEQUENCE: 25

Ile Gly Gly Val Gly Gly
 1               5

<210> SEQ ID NO 26
<211> LENGTH: 6
<212> TYPE: PRT
<213> ORGANISM: mammalian

<400> SEQUENCE: 26

Val Ala Pro Gly Val Gly
 1               5

<210> SEQ ID NO 27
<211> LENGTH: 5
<212> TYPE: PRT
<213> ORGANISM: mammalian

<400> SEQUENCE: 27

Leu Gly Val Gly Gly
 1               5

<210> SEQ ID NO 28
<211> LENGTH: 4
<212> TYPE: PRT
<213> ORGANISM: mammalian

<400> SEQUENCE: 28

Leu Val Pro Gly
 1

<210> SEQ ID NO 29
```

```
<211> LENGTH: 5
<212> TYPE: PRT
<213> ORGANISM: mammalian

<400> SEQUENCE: 29

Phe Arg Ala Ala Ala
 1               5

<210> SEQ ID NO 30
<211> LENGTH: 6
<212> TYPE: PRT
<213> ORGANISM: mammalian

<400> SEQUENCE: 30

Val Gly Gly Val Pro Gly
 1               5

<210> SEQ ID NO 31
<211> LENGTH: 5
<212> TYPE: PRT
<213> ORGANISM: mammalian

<400> SEQUENCE: 31

Phe Gly Pro Gly Gly
 1               5

<210> SEQ ID NO 32
<211> LENGTH: 5
<212> TYPE: PRT
<213> ORGANISM: mammalian

<400> SEQUENCE: 32

Val Gly Val Pro Gly
 1               5

<210> SEQ ID NO 33
<211> LENGTH: 6
<212> TYPE: PRT
<213> ORGANISM: mammalian

<400> SEQUENCE: 33

Val Leu Pro Gly Ala Gly
 1               5

<210> SEQ ID NO 34
<211> LENGTH: 5
<212> TYPE: PRT
<213> ORGANISM: mammalian
<220> FEATURE:
<223> OTHER INFORMATION: Xaa, position 4 is hydroxyproline

<400> SEQUENCE: 34

Val Gly Leu Xaa Gly
 1               5

<210> SEQ ID NO 35
<211> LENGTH: 5
<212> TYPE: PRT
<213> ORGANISM: mammalian

<400> SEQUENCE: 35

Leu Gly Val Gly Ala
 1               5

<210> SEQ ID NO 36
```

```
<211> LENGTH: 4
<212> TYPE: PRT
<213> ORGANISM: mammalian

<400> SEQUENCE: 36

Ala Phe Pro Gly
 1

<210> SEQ ID NO 37
<211> LENGTH: 5
<212> TYPE: PRT
<213> ORGANISM: mammalian

<400> SEQUENCE: 37

Ala Phe Pro Gly Ala
 1               5

<210> SEQ ID NO 38
<211> LENGTH: 5
<212> TYPE: PRT
<213> ORGANISM: mammalian

<400> SEQUENCE: 38

Val Gly Ile Pro Ala
 1               5

<210> SEQ ID NO 39
<211> LENGTH: 6
<212> TYPE: PRT
<213> ORGANISM: mammalian

<400> SEQUENCE: 39

Val Gly Gly Ile Pro Thr
 1               5

<210> SEQ ID NO 40
<211> LENGTH: 7
<212> TYPE: PRT
<213> ORGANISM: mammalian

<400> SEQUENCE: 40

Val Gly Val Gly Val Pro Gly
 1               5

<210> SEQ ID NO 41
<211> LENGTH: 6
<212> TYPE: PRT
<213> ORGANISM: mammalian

<400> SEQUENCE: 41

Leu Gly Pro Gly Val Gly
 1               5

<210> SEQ ID NO 42
<211> LENGTH: 4
<212> TYPE: PRT
<213> ORGANISM: mammalian
<220> FEATURE:
<221> NAME/KEY: MOD_RES
<222> LOCATION: (4)
<223> OTHER INFORMATION: AMIDATION

<400> SEQUENCE: 42

Val Ala Pro Gln
 1
```

```
<210> SEQ ID NO 43
<211> LENGTH: 4
<212> TYPE: PRT
<213> ORGANISM: mammalian
<220> FEATURE:
<221> NAME/KEY: MOD_RES
<222> LOCATION: (1)
<223> OTHER INFORMATION: ACETYLATION

<400> SEQUENCE: 43

Val Val Pro Gln
 1

<210> SEQ ID NO 44
<211> LENGTH: 6
<212> TYPE: PRT
<213> ORGANISM: mammalian
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (6)
<223> OTHER INFORMATION: AMIDATION

<400> SEQUENCE: 44

Gly Ala Val Val Pro Gln
 1               5

<210> SEQ ID NO 45
<211> LENGTH: 5
<212> TYPE: PRT
<213> ORGANISM: mammalian

<400> SEQUENCE: 45

Ala Val Val Pro Gln
 1               5

<210> SEQ ID NO 46
<211> LENGTH: 6
<212> TYPE: PRT
<213> ORGANISM: mammalian

<400> SEQUENCE: 46

Gly Ala Val Val Pro Gln
 1               5

<210> SEQ ID NO 47
<211> LENGTH: 5
<212> TYPE: PRT
<213> ORGANISM: mammalian
<220> FEATURE:
<221> NAME/KEY: MOD_RES
<222> LOCATION: (5)
<223> OTHER INFORMATION: AMIDATION

<400> SEQUENCE: 47

Ala Val Val Pro Gln
 1               5

<210> SEQ ID NO 48
<211> LENGTH: 6
<212> TYPE: PRT
<213> ORGANISM: mammalian
<220> FEATURE:
<221> NAME/KEY: MOD_RES
<222> LOCATION: (6)
```

```
<223> OTHER INFORMATION: AMIDATION

<400> SEQUENCE: 48

Gly Ala Val Val Pro Gln
 1               5

<210> SEQ ID NO 49
<211> LENGTH: 6
<212> TYPE: PRT
<213> ORGANISM: mammalian

<400> SEQUENCE: 49

Cys Val Val Pro Gln Cys
 1               5

<210> SEQ ID NO 50
<211> LENGTH: 7
<212> TYPE: PRT
<213> ORGANISM: mammalian

<400> SEQUENCE: 50

Cys Ala Val Val Pro Gln Cys
 1               5

<210> SEQ ID NO 51
<211> LENGTH: 8
<212> TYPE: PRT
<213> ORGANISM: mammalian

<400> SEQUENCE: 51

Cys Gly Ala Val Val Pro Gln Cys
 1               5

<210> SEQ ID NO 52
<211> LENGTH: 6
<212> TYPE: PRT
<213> ORGANISM: mammalian

<400> SEQUENCE: 52

Cys Val Val Pro Gln Cys
 1               5

<210> SEQ ID NO 53
<211> LENGTH: 7
<212> TYPE: PRT
<213> ORGANISM: mammalian

<400> SEQUENCE: 53

Cys Ala Val Val Pro Gln Cys
 1               5

<210> SEQ ID NO 54
<211> LENGTH: 8
<212> TYPE: PRT
<213> ORGANISM: mammalian

<400> SEQUENCE: 54

Cys Gly Ala Val Val Pro Gln Cys
 1               5

<210> SEQ ID NO 55
<211> LENGTH: 4
<212> TYPE: PRT
<213> ORGANISM: mammalian
```

```
<400> SEQUENCE: 55

Val Val Pro Asn
  1

<210> SEQ ID NO 56
<211> LENGTH: 5
<212> TYPE: PRT
<213> ORGANISM: mammalian

<400> SEQUENCE: 56

Ala Val Val Pro Asn
  1               5

<210> SEQ ID NO 57
<211> LENGTH: 6
<212> TYPE: PRT
<213> ORGANISM: mammalian

<400> SEQUENCE: 57

Gly Ala Val Val Pro Asn
  1               5

<210> SEQ ID NO 58
<211> LENGTH: 5
<212> TYPE: PRT
<213> ORGANISM: mammalian
<220> FEATURE:
<221> NAME/KEY: MOD_RES
<222> LOCATION: (5)
<223> OTHER INFORMATION: AMIDATION

<400> SEQUENCE: 58

Ala Val Val Pro Asn
  1               5

<210> SEQ ID NO 59
<211> LENGTH: 6
<212> TYPE: PRT
<213> ORGANISM: mammalian
<220> FEATURE:
<221> NAME/KEY: MOD_RES
<222> LOCATION: (6)
<223> OTHER INFORMATION: AMIDATION

<400> SEQUENCE: 59

Gly Ala Val Val Pro Asn
  1               5

<210> SEQ ID NO 60
<211> LENGTH: 6
<212> TYPE: PRT
<213> ORGANISM: mammalian

<400> SEQUENCE: 60

Cys Val Val Pro Asn Cys
  1               5

<210> SEQ ID NO 61
<211> LENGTH: 7
<212> TYPE: PRT
<213> ORGANISM: mammalian

<400> SEQUENCE: 61

Cys Ala Val Val Pro Asn Cys
  1               5
```

```
<210> SEQ ID NO 62
<211> LENGTH: 8
<212> TYPE: PRT
<213> ORGANISM: mammalian

<400> SEQUENCE: 62

Cys Gly Ala Val Val Pro Asn Cys
  1               5

<210> SEQ ID NO 63
<211> LENGTH: 6
<212> TYPE: PRT
<213> ORGANISM: mammalian

<400> SEQUENCE: 63

Cys Val Val Pro Asn Cys
  1               5

<210> SEQ ID NO 64
<211> LENGTH: 7
<212> TYPE: PRT
<213> ORGANISM: mammalian

<400> SEQUENCE: 64

Cys Ala Val Val Pro Asn Cys
  1               5

<210> SEQ ID NO 65
<211> LENGTH: 8
<212> TYPE: PRT
<213> ORGANISM: mammalian

<400> SEQUENCE: 65

Cys Gly Ala Val Val Pro Asn Cys
  1               5

<210> SEQ ID NO 66
<211> LENGTH: 8
<212> TYPE: PRT
<213> ORGANISM: mammalian

<400> SEQUENCE: 66

Leu Gly Ala Gly Gly Ala Gly Val
  1               5

<210> SEQ ID NO 67
<211> LENGTH: 9
<212> TYPE: PRT
<213> ORGANISM: mammalian

<400> SEQUENCE: 67

Leu Gly Ala Gly Gly Ala Gly Val Leu
  1               5

<210> SEQ ID NO 68
<211> LENGTH: 8
<212> TYPE: PRT
<213> ORGANISM: mammalian
<220> FEATURE:
<221> NAME/KEY: MOD_RES
<222> LOCATION: (8)
<223> OTHER INFORMATION: AMIDATION

<400> SEQUENCE: 68

Leu Gly Ala Gly Gly Ala Gly Val
```

```
       1               5

<210> SEQ ID NO 69
<211> LENGTH: 9
<212> TYPE: PRT
<213> ORGANISM: mammalian
<220> FEATURE:
<221> NAME/KEY: MOD_RES
<222> LOCATION: (9)
<223> OTHER INFORMATION: AMIDATION

<400> SEQUENCE: 69

Leu Gly Ala Gly Gly Ala Gly Val Leu
  1               5

<210> SEQ ID NO 70
<211> LENGTH: 9
<212> TYPE: PRT
<213> ORGANISM: mammalian

<400> SEQUENCE: 70

Cys Leu Gly Ala Gly Gly Ala Gly Cys
  1               5

<210> SEQ ID NO 71
<211> LENGTH: 10
<212> TYPE: PRT
<213> ORGANISM: mammalian

<400> SEQUENCE: 71

Cys Leu Gly Ala Gly Gly Ala Gly Val Cys
  1               5                  10

<210> SEQ ID NO 72
<211> LENGTH: 11
<212> TYPE: PRT
<213> ORGANISM: mammalian

<400> SEQUENCE: 72

Cys Leu Gly Ala Gly Gly Ala Gly Val Leu Cys
  1               5                  10

<210> SEQ ID NO 73
<211> LENGTH: 9
<212> TYPE: PRT
<213> ORGANISM: mammalian

<400> SEQUENCE: 73

Cys Leu Gly Ala Gly Gly Ala Gly Cys
  1               5

<210> SEQ ID NO 74
<211> LENGTH: 10
<212> TYPE: PRT
<213> ORGANISM: mammalian

<400> SEQUENCE: 74

Cys Leu Gly Ala Gly Gly Ala Gly Val Cys
```

-continued

```
         1               5              10
```

<210> SEQ ID NO 75
<211> LENGTH: 11
<212> TYPE: PRT
<213> ORGANISM: mammalian

<400> SEQUENCE: 75

```
Cys Leu Gly Ala Gly Gly Ala Gly Val Leu Cys
 1               5                  10
```

ELASTIN PEPTIDE ANALOGS AND METHODS OF USING SAME

CROSS-REFERENCE TO RELATED APPLICATION

This application is a continuation-in-part of U.S. application Ser. No. 09/039,308 filed Mar. 13, 1998, now U.S. Pat. No. 6,069,129, and of International Application No. PCT/US99/05496 filed Mar. 12, 1999.

BACKGROUND OF THE INVENTION

1. Field of the Invention

The present invention relates to compositions which are particularly suitable as therapeutics, pharmaceutics, and/or cosmetics. The compositions of the present invention preferably include a peptide or peptide-like compound which simulate the effect of elastin. Preferably, compounds of the present invention are substantially homologous or analogous with a portion of mammalian elastin, even more preferably with fragments of elastin endogenous to the tissue of the mammal being treated. It is preferable that the peptide or peptide-like compound(s) of the present invention are i:at a therapeutically effective concentration and/or are an active ingredient of a pharmaceutic, therapeutic and/or cosmetic composition. The peptide or peptide-like compound(s) of the present invention appear to aid the elasticity and/or turgor of the skin. Another aspect of the present invention is a method of administering the compositions of the present invention to achieve a therapeutic, pharmaceutic, or cosmetic effect.

2. Background and Description of the Related Art

Elastin, a highly cross-linked complex polypeptide, is a major component of elastic fibers present in the tissue of animals. Elastin is found in most connective tissues in conjunction with collagen and polysaccharides. Relatively large amounts of elastin are also found in the walls of blood vessels, particularly in the arch of the aorta near the heart, as well as in ligaments. Elastin is present in lesser amounts in skin, tendons, and loose connective tissue. In normal mammalian skin, specifically human skin, elastic tissue proteins represent a relatively small fraction of the total dermal proteins, but play a very important role in maintaining the tone, structure, and turgor of the skin.

Elastin fibers are capable of stretching to several times their length and then rapidly returning to their original size upon release of tension. Hence, elastin contributes to the physiological elasticity of tissue. It has been found, for instance, that a loss of elasticity in the skin is associated with decrease in the tone and turgor of the skin. It is speculated that the decrease in skin tone and turgor occurs through degradation of elastin and collagen. Attempts have been made to use elastin as a cosmetic agent, however, the dense cross-linked structure of elastin makes it very difficult to solubilize. In fact, elastin is only slightly absorbed by the skin and does not penetrate the skin sufficiently to produce substantial benefits. Attempts to solubihze elastin and create cosmetic agents are described, for example in U.S. Pat. No. 4,327,078.

SUMMARY OF THE PRESENT INVENTION

The present invention is directed to compositions which are pharmaceutic, therapeutic, and/or cosmetic in nature. The composition of the present invention preferably modifies or appears to modify the physical characteristics of the tissue to which it is applied. The composition generally includes a vehicle or carrier for therapeutic, pharmaceutic, or cosmetic administration in which the peptide or peptides are formulated.

The compound(s) which best accomplish an increase or apparent increase in tissue elasticity and turgor are ones which correspond to, are analogous to, or are substantially homologous, with portions of elastin. As used herein, the terms "peptide" or "peptide-like" is not meant to convey any meaning regarding the precursor material or methods utilized to make the compounds. For instance, compounds or compositions contemplated within the present invention are those that mimic the action or functionality of the amino acid containing peptides or peptide-like compounds of the present invention. Computational chemistry can be used to predict structure-function relationship, and compounds thus predicted and synthesized may mimic the structure and function of a particular peptide or peptide-like compound disclosed herein. Additionally, the term "elastin peptide fragment" in either singular or plural form refers to the fact that the peptide or amino acid sequence being discussed: corresponds to; is the biological equivalent of; is analogous with; or is substantially homologous with, a portion of elastin. The term "elastin peptide fragment" is not meant to convey any meaning regarding the source or starting material or method of arriving at the elastin peptide fragment.

It is preferable that the peptides of the present invention are formulated at an effective concentration within the therapeutic, pharmaceutic or cosmetic composition. The therapeutically effective concentration is preferably in a range of about 0.0002% to about 90% by weight of the peptide or peptide-like compound, more preferably in a range of about 0.05% to about 50% peptide, even more preferably in a range of about 0.5% to about 10% peptide, and even more preferably about 1.5% peptide. The therapeutic composition of the present invention can be formulated as a cosmetic preparation to be applied topically to a patient's skin, such as in an emulsion, lotion, spray, powder, ointment, cream, or foam or in other suitable pharmaceutical vehicles or carriers commonly known in the art for other types of administration (e.g., oral or subcutaneous). The delivery system of the present invention is preferably a topical delivery system but also may be a subcutaneous, transcutaneous, oral, nasal, aerosol, or patch. The peptide(s) or peptide-like compound(s) of the present invention have many other applications, for example they may also be used to coat surgical devices such as stents and the like.

The present invention is also directed to a method of enhancing the functionality, tone, turgor, and/or elasticity of the tissue to which it is administered by administrating effective amounts of a peptide to the tissue. When treating skin, the appearance of the skin is enhanced. It is believed that this enhancement is a consequence of improving the elasticity of the skin. It is preferable that the administration step be comprised of a number of separate steps which are repeated over a predetermined time (e.g., twice daily). It is preferable that the predetermined time exceeds one week of daily administration of the compound, more preferably two weeks, and most preferably at least a month of daily topical application (with twice daily of the peptide administration over the month being even more preferable).

The present invention is also directed to a composition being comprised of a peptide selected from the group consisting of SEQ ID 1, SEQ ID 2, SEQ ID 3, SEQ ID 4, SEQ ID 5, SEQ ID 6, SEQ ID 7, SEQ ID 8, SEQ ID 9, SEQ ID 10, SEQ ID 11, SEQ ID 12, SEQ ID 13, SEQ ID 14, SEQ ID 15, SEQ ID 16, SEQ ID 17, SEQ ID 18, SEQ ID 19, SEQ ID 20, SEQ ID 21, SEQ ID 22, SEQ ID 23, SEQ ID 24, SEQ ID 25, SEQ ID 26, SEQ ID 27, SEQ ID 28, SEQ ID 29, SEQ ID 30, SEQ ID 31, SEQ ID 32, SEQ ID 33, SEQ ID 34, SEQ ID 35, SEQ ID 36, SEQ ID 37, SEQ ID 38, SEQ ID 39, SEQ ID 40, SEQ ID 41, SEQ ID 42, SEQ ID 43, SEQ ID 44, SEQ ID 45, SEQ ID 46, SEQ ID 47, SEQ ID 48, SEQ ID 49, SEQ ID 50, SEQ ID 51, SEQ ID 52, SEQ ID 53, SEQ ID 54, SEQ ID 55, SEQ ID 56, SEQ ID57, SEQ ID 58, SEQ ID 59, SEQ ID 60, SEQ ID 61, SEQ ID 62, SEQ ID 63, SEQ ID 64, SEQ ID 65, SEQ ID 66, SEQ ID 67, SEQ ID 68, SEQ ID 69, SEQ ID 75, SEQ ID 71, SEQ ID 72, SEQ ID 73, SEQ ID 74 and SEQ ID 75 and their biological equivalents.

Another embodiment of the present invention is directed to peptide having a formula of $R_1$-Leucine-Glycine-$R_2$, wherein $R_1$ is an amino portion modified to include an amine, amide, or amino acid sequence having 1–10 amino acids and $R_2$ is a carboxy portion modified to include an amide, ester, or carboxy terminus sequence having 1–10 amino acids.

Another embodiment of the present invention is directed to peptide having a formula of $R_1$-Leucine-Glycine-Alanine-Glycine-Glycine-Alanine-Glycine-$R_2$, wherein $R_1$ is an amino portion modified to include an amine, amide, or amino acid sequence having 1–10 amino acids and $R_2$ is a carboxy portion modified, to include an amide, ester, or carboxy terminus sequence having 1–10 amino acids.

Further, the composition of the invention and their biological equivalents may be suitable as a therapeutic, pharmaceutic or cosmetic to enhance elastin production and may also be used to treat a variety of diseases or conditions selected from the group consisting of conditions or diseases of the skin, tendons, sheaths and/or bone, hair, lip, back or spine, brain or nervous system, lautoimmune system, lungs, muscle, joints, nails, blood vessels/lymphatics, breast, cartilage, ear, eye, genito-urinary tract, gastrointestinal tract, immunologic systems, ulcerative, blood vessels/heart (e.g. hypertension), and other body systems.

BRIEF DESCRIPTION OF THE DRAWINGS

The features, aspects, and advantages of the present invention will become better understood in light of the following description, appended claims, and accompanying drawings wherein:

DETAILED DESCRIPTION OF THE PRESENT INVENTION

Figure 1:
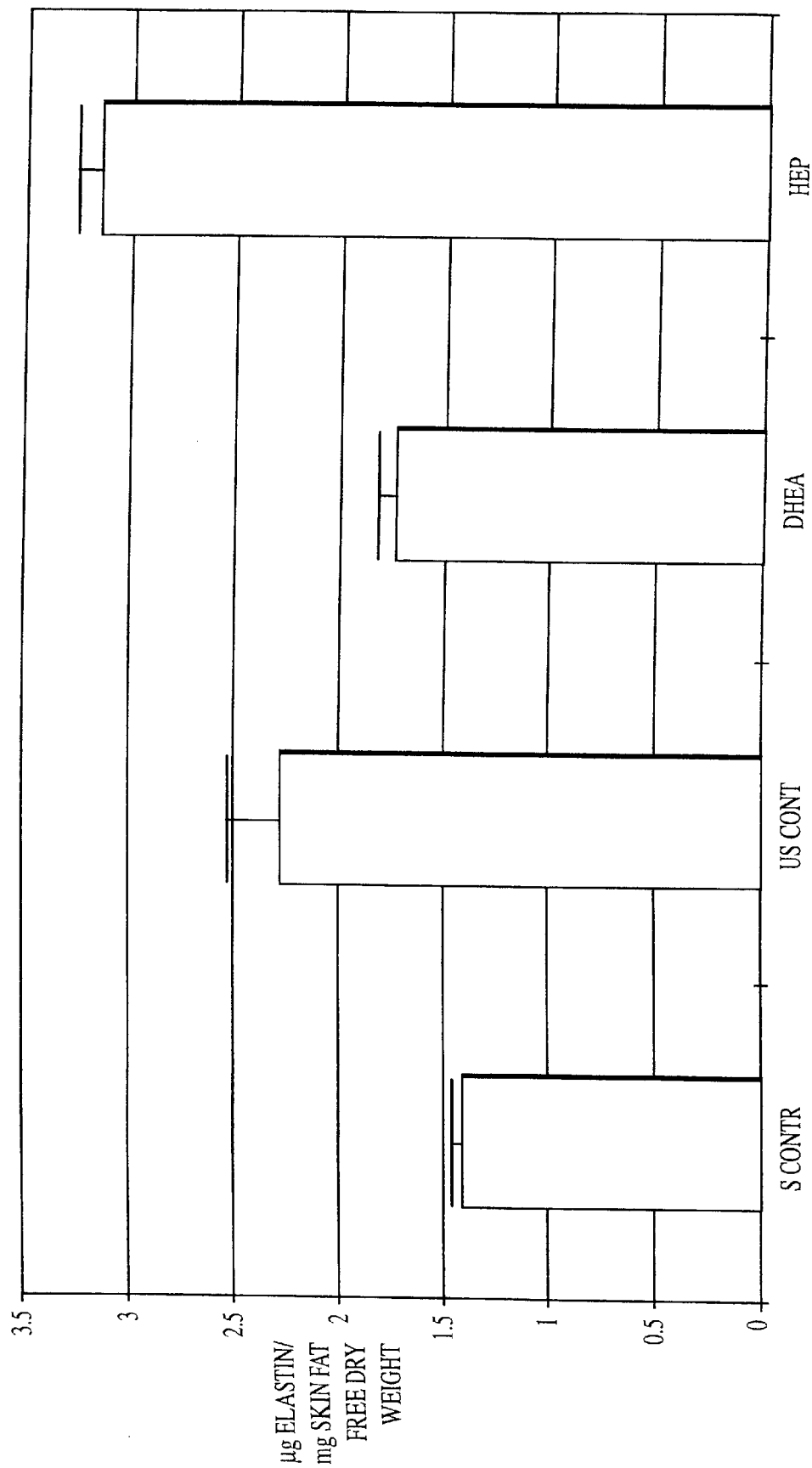
FIG. 1 is a bar graph illustrating increased elastin production as a result of application of select compounds of the present invention to mammalian skin.
Figure 2A:
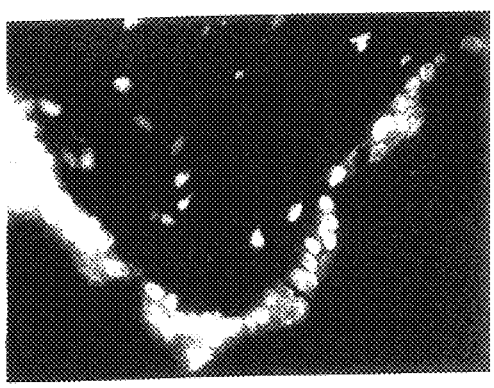
FIG. 2 is a micrograph illustrating the microvascular response of the skin tissue with peptides of the present invention.
Figure 2B:
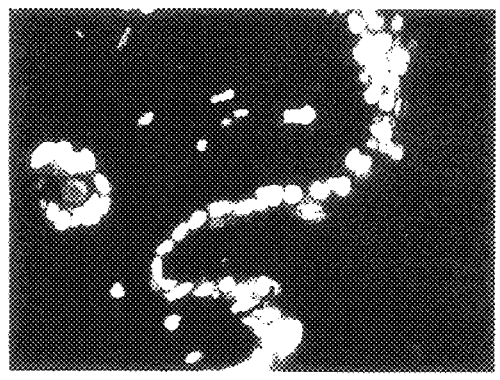
Figure 2C:
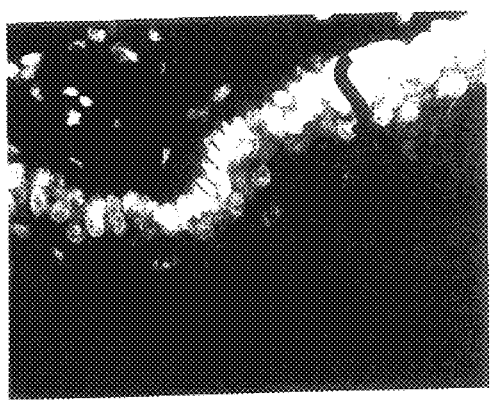
Figure 2D:
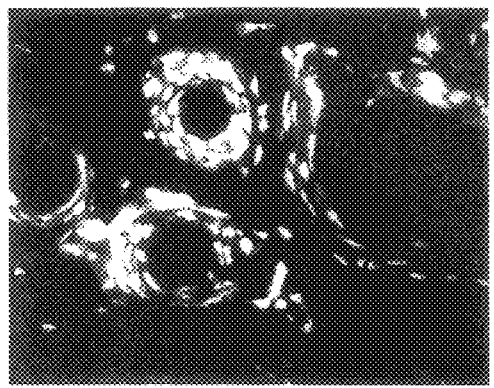

So that the invention described herein may be more fully understood, the following detailed description is set forth. The description is in no way meant to limit the breadth of the claims, but rather to specifically point out novel aspects of the present invention.

The present invention relates to compositions which are useful in increasing functionality, elasticity, tone, turgor, and/or appearance of tissue. The present invention is also directed to administering therapeutically effective concentrations of the compositions.

As used herein, the term "subject" or "patient" means any mammal, including humans, in which elastin is utilized for proper tissue function or appearance. The methods herein for use contemplate prophylactic, cosmetic, and curative use.

As used herein, the term "about" means plus or minus 10% of the numerical value of the number with which it is being used. Therefore, about 50% means in the range of 45%–55%. As used herein, the term "Dalton" (or "Da") refers to the unit of mass which is equivalent to the mass of a hydrogen atom ($1.66 \times 10^{-24}$ gram). Generally speaking, the term "tissue" refers to any aggregation of similarly specialized cells which are united in the performance of a particular function. The term "tissue", as usually used herein, refers to tissue which includes elastin as part of its preferred structure and/or function. For example, connective tissue which is made up of, among other things, collagen fibrils and elastin fibrils satisfies the definition of "tissue". Additionally, since elastin appears to be inherently involved in the visco-elasticity of blood vessels, veins, and arteries, these would be encompassed in the definition of "tissue". The term "skin" is encompassed by the term "tissue" but specifically means the outer integument or covering of the body, including the dermis and the epidermis which rests upon subcutaneous tissue.

"Providing" when used in conjunction with a therapeutic, pharmaceutic, or cosmetic means to administer an agent directly into or onto a target tissue or to administer a therapeutic to a patient whereby the therapeutic positively impacts the tissue to which it is targeted (either in a prophylactic, curative or cosmetic manner). Thus, as used herein, the term "providing", when used in conjunction with elastin peptide fragment, can include, but is not limited to, providing an elastin peptide fragment into or onto the target tissue; providing an elastin peptide fragment systemically to a patient by, e.g., intravenous injection whereby the therapeutic agent reaches the target tissue; providing an elastin peptide fragment in the form of the encoding sequence thereof to the target tissue (e.g., by so-called gene-therapy techniques) whereby the elastin peptide fragment is expressed within the target tissue. Details on techniques for formulation and administration of pharmaceuticals may be found in the latest edition of *Remington's Pharmaceutical Sciences* (Mack Publishing Co, Easton Pa.). Although local topical delivery is desirable, there are other acceptable means of delivery, for example: oral, parenteral, aerosol, intramuscular, subcutaneous, transcutaneous, intamedullary, intrathecal, intraventricular, intravenous, intraperitoneal, or intranasal administration.

As used herein, the term "therapeutic" means an agent utilized to treat, combat, ameliorate, prevent or improve a condition or disease of a patient. A particular condition treated in the present invention is deficient elastin in a particular tissue, that is, a need in the tissue for more elastin. As it applies to skin, "therapy" is often measured by turgor, tone, appearance, degree of wrinkles, and youthfulness. As the term applies to blood vessels it may be measured by the degree of elasticity or proper vasomotor response (vasodilatation/vasoconstriction) of the vessel. Accordingly, therapeutic treatment of blood vessels may have implications in diseases associated with visco-elasticity, including hypertension, arteriosclerosis, angina, angiogenesis, myocardial infarction, coronary thrombosis, restenosis post angioplasty, and chronic obstructive pulmonary disease.

Finally, the term "cosmetic," as used herein, refers to a beautifying substance or preparation which preserves, restores, bestows, simulates, or enhances the appearance of bodily beauty, specifically as it relates to the appearance of tissue or skin.

The compounds and compositions of the present invention may also be useful as an agent for modifying tissue, especially skin. The term "modify" is used to convey that the present invention changes either the appearance, form, characteristics and/or the physical attributes of the tissue to which it is being provided, applied or administered. The change in form can be reflected in any of the following alone or in combination: enhanced appearance of the skin; increased softness of the skin; increased turgor of the skin; increased texture of the skin; increased elasticity of the skin; decreased wrinkle formation and increased endogenous elastin production in the skin.

Elastin can be used as starting material in the digestion or cleavage methods described herein. This elastin can be derived from a number of sources known in the art. The sequences of the present invention can either be isolated from the digestion pool (and chemically modified if desired) or the peptides may be synthesized with a peptide sequencer. A particularly useful source of elastin is ligamentum nuchae. Ligamentum nuchae contains large amounts of elastin (approximately 70% of the dry weight of this ligament is elastin), especially in proportion to the amount of collagen. Due to the relatively high elastin content and relatively low collagen content, ligamentum nuchae is an ideal starting material to use in deriving the elastin peptide fragments of the present invention. The ligamentum nuchae may be cleaned first using a procedure similar to that disclosed in U.S. Pat. No. 5,028,695, the cleaning portion of which is incorporated herein by reference thereto. Although a preferred source of starting elastin is ligamentum nuchae, other ligaments, tendons, connective tissue, tissue, and synthetic sources may also be used. For example, the arteries and lungs, and other animal tissue, especially those which have significant amounts of elastin, can be used (e.g., rat, sheep, and porcine aorta can be used as a source of elastin as described in L. B. Sandberg, *Connective Tissue Research*, 1990, Vol. 25, pp. 139–148, incorporated herein in its entirety by reference thereto). Also, elastin from different sources, or elastin and collagen from the same or different sources could be mixed together to produce a particular advantageous mix suitable for digestion or hydrolytic cleavage.

In one embodiment of the present invention, the ligament extraction process is comprised of taking dissected ligamentum nuchae ligaments and removing as much fat and excess connective tissue as possible. These "clean" ligaments are then chopped into about one centimeter square (1 cm$^2$) pieces and washed with doubly distilled water ("DDW"). The clean ligaments are then placed on a metal mortar, pre-chilled to −20° F. and liquid nitrogen is added to freeze the tissue. The ligaments are then minced or pulverized with the appropriate tool and re-suspended in 1% aqueous NaCl at a ratio of about 100 grams of tissue to about three liters of 1% aqueous NaCl and homogenized in a Warning blender at high speed for 30–60 seconds. The homogenized ligament is transferred to a four-liter beaker and stirred overnight at 4° C. on a magnetic stirrer, after which it is centrifuged at 32,500×G and the supernatant is checked for protein content using the Biuret method for protein determination. The Biuret reaction is done by mixing 2 milliliters of extract with 3 milliliters of reagent and reading immediately either by simple visual inspection or at 540 nanometers on a spectrophotometer to determine the protein concentration of the supernatant. The supernatant is then discarded. The pellet (referred to hereinafter as the elastin pellet) is resuspended in 1% aqueous NaCl and homogenized. The process of homogenizing in a Warning blender, stirring overnight and centrifuging are repeated three to four times until the supernatant is Biuret negative. After centrifugation, the elastin pellet is resuspended in DDW and autoclaved 30 psi for six hours. The resuspended elastin pellet is centrifuged again and the supernatant is tested for protein content via the Biuret method. The elastin is washed with boiling DDW and then with DDW at room temperature and the washes are tested for protein content via the Biuret method. If the washes are Biuret negative, the elastin pellet is dried with chloroform/methanol solution at a ratio of 2 parts chloroform to 1 part methanol. If the Biuret test is positive, the six hour autoclave procedure with wash step is repeated until the Biuret test is negative. Finally, the elastin residue is washed with five volumes of pure methanol and air-dried at room temperature. The elastin residue is transferred to a desiccator and dried over $P_2O_5$ for 24 hours until the weight of the elastin residue is stable. The elastin residue is then milled in a Willey mill through a 40-mesh screen followed by a 60-mesh screen.

For the thermolysin digestion, three times re-crystallized thermolysin product from CalBiochem (10394 Pacific Center Court, San Diego, Calif. 92121) was used. The thermolysin preparation contains sufficient calcium to ensure maximal activity of the enzyme. The thermolysin digestion is done as follows: a waterbath is brought to a 55° C. temperature with a rotary shaker and five grams of the finely milled largely insoluble elastin residue is hydrated with one liter of DDW for fifteen minutes at room temperature. After hydration, the one liter DDW which contains the five grams of elastin is placed in the 55° C. bath and the pH of the elastin/water mixture is brought to a pH between 7–8 with 10% methylamine. Fifty milligrams of thermolysin (bacillus thermoproteolyticus) is added directly to the elastin water mixture. The thermolysin contains about 60% protein (60.2%), about 13% (13.2%) sodium acetate, and about 25% (25.3%) calcium acetate, with a specific activity of about 8,720 I.U./mg dry weight. The pH of the elastin water mixture is monitored with a pH meter or pH stat and adjusted with 10% methylamine to keep the pH between 6.8 and 7.5. The digestion is allowed to continue for 75 minutes and then concentrated hydrochloric acid is added to adjust the pH to 3.0 to terminate the digestion.

After digestion is terminated, the digested product is preferably filtered through a PM 10 Diaflow 10,000 molecular weight cut-off ultra-filtration membrane to filter out any protein or peptides exceeding about 10,000 Da molecular weight. The resulting supernatant is a derived composition comprised of peptides having a molecular weight of less than about 10,000 Da.

Table 1 is a list of peptide sequences which, either alone or in combination, in the supernatant exhibit desirable characteristics.

TABLE I

| SEQ # | PEPTIDE | MOL WT | NAME (N- to C-terminal) |
|---|---|---|---|
| 1. | AVG | 245 | Alanine-Valine-Glycine |
| 2. | VGAG | 302 | Valine-Glycine-Alanine-Glycine |
| 3. | IGG | 302 | Isoleucine-Glycine-Glycine |
| 4. | LG | 188 | Leucine-Glycine |
| 5. | IGAG | 316 | Isoleucine-Glycine-Alanine-Glycine |
| 6. | LGG | 245 | Leucine-Glycine-Glycine |
| 7. | VAPG | 342 | Valine-Alanine-Proline-Glycine |
| 8. | LGPG | 342 | Leucine-Glycine-Proline-Glycine |
| 9. | LGAG | 316 | Leucine-Glycine-Alanine-Glycine |
| 10. | VGPG | 328 | Valine-Glycine-Proline-Glycine |
| 11. | FGPG | 376 | Phenylalanine-Glycine-Proline-Glycine |
| 12. | VGPQ | 399 | Valine-Glycine-Proline-Glutamine |

TABLE I-continued

| SEQ # | PEPTIDE | MOL WT | NAME (N- to C-terminal) |
|---|---|---|---|
| 13. | LGA | 259 | Leucine-Glycine-Alanine |
| 14. | VGPA | 342 | Valine-Glycine-Proline-Alanine |
| 15. | VVPG | 370 | Valine-Valine-Proline-Glycine |
| 16. | AVPG | 342 | Alanine-Valine-Proline-Glycine |
| 17. | VVPQ | 441 | Valine-Valine-Proline-Glutamine |
| 18. | VAARPG | 569 | Valine-Alanine-Alanine-Arginine-Proline-Glycine |
| 19. | LGAGGAG | 501 | Leucine-Glycine-Alanine-Glycine-Glycine-Alanine-Glycine |
| 20. | AIPG | 356 | Alanine-Isoleucine-Proline-Glycine |
| 21. | LGPGG | 399 | Leucine-Glycine-Proline-Glycine-Glycine |
| 22. | AAAQA | 430 | Alanine-Alanine-Alanine-Glutamine-Alanine |
| 23. | VGVHypG | 444 | Valine-Glycine-Valine-Hydroxyproline-Glycine |
| 24. | VYPGG | 491 | Valine-Tyrosine-Proline-Glycine-Glycine |
| 25. | IGGVGG | 458 | Isoleucine-Glycine-Glycine-Valine-Glycine-Glycine |
| 26. | VAPGVG | 498 | Valine-Alanine-Proline-Glycine-Valine-Glycine |
| 27. | LGVGG | 401 | Leucine-Glycine-Valine-Glycine-Glycine |
| 28. | VLPG | 384 | Valine-Leucine-Proline-Glycine |
| 29. | FRAAA | 534 | Phenylalanine-Arginine-Alanine-Alanine-Alanine |
| 30. | VGGVPG | 484 | Valine-Glycine-Glycine-Valine-Proline-Glycine |
| 31. | FGPGG | 433 | Phenylalanine-Glycine-Proline-Glycine-Glycine |
| 32. | VGVPG | 427 | Valine-Glycine-Valine-Proline-Glycine |
| 33. | VLPGAG | 512 | Valine-Leucine-Proline-Glycine-Alanine-Glycine |
| 34. | VGLHypG | 458 | Valine-Glycine-Leucine-Hydroxyproline-Glycine |
| 35. | LGVGA | 415 | Leucine-Glycine-Valine-Glycine-Alanine |
| 36. | AFPG | 390 | Alanine-Phenylalanine-Proline-Glycine |
| 37. | AFPGA | 461 | Alanine-Phenylalanine-Proline-Glycine-Alanine |
| 38. | VGIPA | 455 | Valine-Glycine-Isoleucine-Proline-Alanine |
| 39. | VGGIPT | 542 | Valine-Glycine-Glycine-Isoleucine-Proline-Threonine |
| 40. | VGVGVPG | 583 | Valine-Glycine-Valine-Glycine-Valine-Proline-Glycine |
| 41. | LGPGVG | 498 | Leucine-Glycine-Proline-Glycine-Valine-Glycine |

*SEQ IDs 23 and 32 appear to be a common sequence because Proline hydroxylation is a post-translational event.

The elastin peptide fragment/water mixture (inclusive of SEQ IDs 1–41) which is obtained upon digestion with thermolysin described above is flash evaporated to dryness and redissolved in a small volume of DDW and if desired is diluted sufficiently with DDW for lyophilization to dryness. In the alternative, rather than redissolving the elastin peptide (s), the filtered product is freeze dried twice, resulting in a powder which contains 30 weight chemically-bound water and very little salt (NaCl).

The method of administering peptides and formulations of the present invention employs any of a number of known administrative routes such as oral, IV, subcutaneous, transcutaneous, and topical administration. A preferred method of the present invention employs a pharmaceutical or cosmetic composition which enhances the physical appearance of and/or the elasticity of tissue. Compositions of the present invention may be in the form of a peptide or peptides in combination with at least one other agent, such as stabilizing compound, which may be administered in any sterile, bio-compatible pharmaceutical carrier, including, but not limited to, saline, buffered saline, dextrose, and water. The compositions may be administered to a patient alone, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of *Remington's Pharmaceutical Sciences*. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. After pharmaceutical compositions have been prepared, they can be placed in an appropriate container and labeled for treatment of an indicated condition. Such labeling would include amount, frequency, and method of administration.

It is believed that one of the advantages of the present invention is the apparent ability of the peptides or peptide-like compounds of the present invention to penetrate the skin. Advantageously, the present invention uses peptides which have a molecular weight of less than about 10,000 Da, more preferably less than about 3,000 Da, even more preferably less than 1,000 Da. Thus, the peptides of the present invention would appear to meet the criteria for absorption by the skin upon application.

The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. U.S. Pat. No. 4,327,078, which was referenced earlier, is illustrative of the different types of topical administrations which may be employed to administer a soluble elastin-based derivative, and is incorporated herein by reference for this purpose.

The peptide or peptides of the present invention, as well as their corresponding therapeutic compositions are expected to have a variety of important applications. The following descriptions provide a brief summary of the conditions these peptide(s) are likely to benefit.

Skin conditions: There are many skin conditions and diseases which would benefit from elastin treatment. Beyond the obvious cosmetic applications (i.e., increased tone, turgor, and appearance), enhanced elastin production will produce long-term beneficial results. For example, the inherited disease Scleraderma is characterized by a thickening and stiffening of the skin, and cutaneous ulcers due to the overproduction of collagen (there are a number of diseases which involve overproduction of collagen and which seem to have an adverse effect on elastin production/content and compromise the tissue). This disease can also have systemic effects on organs and blood vessels. The stiffness and difficulty in motion along with the cutaneous ulcers would benefit greatly from incorporation of elastin into the skin. A similarly positive outcome would be expected with the treatment of lupus and rheumatoid related skin changes which are generally collagen-vascular diseases involving a decrease in elastin.

Other skin conditions would appear to benefit from the present invention. Conditions and problems such as acne rosacea, acne vulgaris, aging skin with vascular fragility, burn treatment, scar contractures from burns, radiation burns, purities (or chronic itching), psoriasis, urticaria (commonly referred to as hives), xerosis (abnormal dryness of the skin, eyes or mouth), vesicular dermatoses, cracked fingers and feet, drug eruptions (from an allergic reaction), epidermolysis (a skin condition where the epidermis is in a loosened state, often with the formation of blebs and bullae either spontaneously or after trauma), and erythema multiforme would benefit from treatment with the elastin peptide(s) of the present invention.

Additionally, there are heritable skin disorders such as cutis laxa and EDS or Ehlers Danlos Syndrome (a group of connective tissue disorders in which the skin hangs in loose pendulous folds believed to be caused by decreased elastic tissue formation as well as an abnormality in elastin formation or an excess of collagen), EDS, elastoderma, progeria, and pseudoxanthoma elasticum (an inherited disorder in which elastic fibers found in many tissues slowly become calcified) which would benefit from an increase in elastin in the affected tissues.

It is believed that the application of the elastin peptides of the present invention would result in an increase in tissue elastin and may provide effective treatment for serious diseases such as pemphigus.

Tendons, Sheaths and Bone: Tendons, sheaths and bone all are comprised in part of elastin. Chronic, painful conditions affecting some of these tissues include carpal tunnel disease, fasciitis, flat feet, and tendonitis. These conditions and similar ones will be improved with increased levels of elastin in the affected tissue. Bone spurs, fascial tears, ligament tears and tendon tears will heal faster with supplemental elastin provided by the elastin peptides of the present invention. These tissues may even become stronger as a result of the expected stimulation of elastin production accompanying this treatment. Additionally, cartilage growth abnormalities may be corrected by application of elastin peptides of the present invention.

Treatment with the elastin peptides of the present invention will also be useful in veterinary medicine for skin ulcerations in livestock such as horses and cattle. Hoof problems can be very painful and problematic for horses and other hoofed animals. Hoof conditions would benefit from increased elastin levels which could be provided and induced by treatment with elastin peptides of the present invention.

Hair: Hair growth, color, and removal can all be improved by treatment with elastin peptides which will make the hair stronger, more shiny, and improve the condition and healing of irritated skin upon removal of unwanted hair. Premature graying of hair may also be due to decreased elastin.

Lips: Chapped lips and chronic dermatitis or inflammation of the lips can be greatly improved upon treatment with elastin peptides of the present invention. Long-term relief would be a potential benefit from the stimulation of endogenous elastin in these tissues.

Back: The breakdown of elastin in the spine can contribute to herniated disks and lead to acute and/or chronic pain. Replacing elastin with peptides of the present invention along with the stimulation of endogenous elastin could result in improved healing of the disk and reduce or eliminate the pain associated with this condition, especially when combined with other treatments, such as steroids.

Brain and nervous system: In nerve compression syndromes, treatment with elastin peptides of the present invention will likely stimulate endogenous elastin production in certain neurological conditions and promote revascularization after stroke and neural tissue transplants. This revascularization could greatly improve the clinical outcome of these treatments.

Autoimmune diseases: Lupus and other rheumatoid related diseases are characterized by localized destruction or degeneration of elastin in tissues throughout the body. These and similar diseases could greatly benefit from treatment with elastin peptides of the present invention which would promote restoration of damaged tissue and even provide long-term benefit from the stimulation of endogenous elastin.

Lungs: Many lung diseases including chronic obstructive pulmonary disease, laryngeal stenosis, pulmonary fibrosis, pulmonary sarcoid and tracheal stenosis are associated with a decrease in elastin, an important component in maintaining the elasticity and proper functioning of the lung. Often, these lung conditions are due to a decrease in particular proteases which normally balance the activity of elastin-degrading proteases, referred to generally as elastases. An example of this type of deficiency is alpha 1 protease inhibitor deficiency. A decrease in elastin due to this type of deficiency causes a breakdown of the lung matrix which is vital for proper lung function. Other factors, such as smoking can also lead to breakdown of the elastin component of the lung matrix.

Muscle: Muscles are often covered with a thin layer of connective tissue which is comprised of elastin and other components such as collagen. Thus, applying peptides of the present invention to muscle tissue would increase muscle tone and the healing of muscle tears and generally strengthen muscles by increasing their elastin content.

Joints: Similarly, joints are comprised of connective tissue, including elastin. In many cases individuals suffer from joint pain and joint abnormalities as a result of inflammatory disease or from wear and tear which all generally result in decreased amounts of elastin present in the connective tissue of joints. Thus, many joint diseases or problems such as athletic joint injuries, torn cartilage and/or ligaments, osteoarthritis, joint pain, rheumatoid arthritis, and stiff joints could benefit from treatment with elastin-peptides of the present invention. These elastin peptides will have the capability to stimulate endogenous elastin in these tissues and may provide substantial and long-term rebuilding and maintenance of the elastin in these tissues.

Nails: Elastin is useful in treating and preventing nail brittleness, split nails, and to enhance the hardness of nails in general. Nails are comprised of flattened epidermal cells and have a high concentration of elastin in the nail bed. Thus, increasing the elastin content of these cells will result in a stronger and more flexible nail.

Blood vessels/lymphatics: Elastin is an important constituent of vessels; therefore, application of elastin to affected tissues in vascular diseases which involve abnormalities of arteries or veins including atherosclerotic occlusive disease, chronic venous insufficiency, diabetic vasculitis (inflammation of a vessel caused by diabetes), fibrotic mediastinitis associated with superior vena cava syndrome (an exuberant inflammatory sclerogenic process of infectious, rheumatic, hemorrhagic, or undetermined origin, often accompanied by obstruction of mediastinal structure, especially the vena cava), varicose veins, temporal arteritis, stasis dermatitis, and lymphedema (including elephantiasis, which is a chronic unilateral or bilateral edema of the extremities due to accumulation of interstitial fluid as a result of the stasis of lymph, which is caused by an obstruction of the lymph vessels).

Breast: Capsule contractures secondary to breast implants are disorders of fibers and are, conditions of fixed high resistance (rigidity) to passive stretch of a muscle. Fibrocystic disease, selected cases of breast cancer where there is tissue loss may also benefit from treatment with elastin peptides.

Cartilage growth: Transformation of hyaline cartilage to elastin cartilage in remaking of structures such as an ear, nose, larynx or any structure in which elastic cartilage would be beneficial, could be aided by treatment with elastin peptides.

Ear: Chronic: serous otitis media and hearing loss secondary to otitis media as well as other diseases causing scarring of the ear drum can benefit from replacement of elastin which can serve to repair scarred ear drum tissue caused by these chronic infections.

Eye: Eye disorders such as diabetic retinitis, retinal hemorrhages associated with pseudoxanthoma elasticum (PXE), macular degeneration, and retinitis pigmentosa all involve abnormalities of the retina which is comprised in part of elastic fibers. PXE is an inherited disorder in which elastic fibers become slowly calcified, producing characteristic changes in the skin, the retina of the eye, and the cardiovascular system. Incorporation of healthy, normal elastin peptides to the retinas of individuals affected by these disorders could improve vision and lead to healing of the retina and prevention of further damage caused by the lack of or presence of malformed elastin is this tissue.

Genito-urinary tract: There are various genito-urinary conditions which are associated with either chronic inflammation or other condition leading to a decrease in elasticity of connective tissue, or with the narrowing of canals or ducts (strictures). The replenishing of elastin or the reversal of the strictures by treatment with elastin and the stimulation of endogenous elastin would benefit a number of genito-urinary conditions including benign prostatic hyperplasia, chronic sclerosing vaginitis, glomerular sclerosis, ureteral stricture, urethral stricture and use with urethral stents, uterine benign fibroids, and vaginal stenosis.

Gastrointestinal tract: A number of GI conditions are the result of chronic inflammation, or abnormal thickening or calcification of GI tissues including anal fissures, chronic pancreatitis, esophageal stenosis, esophageal varicies, hemorrhoids, intestinal adhesions, and pyloric stenosis. Crohn's disease as well as other localized inflammatory/ fibrotic bowel diseases are characterized by a chronic granulomatous inflammatory condition of unknown etiology. Scarring and thickening of the bowel wall frequently leads to intestinal obstruction and the formation of fistula and abscesses. It is likely that supplying elastin to these tissues may improve gastrointestinal function in these patients and restore the normal balance of connective tissue components in the gastrointestinal tract. Similarly, in biliary cirrhosis and fibrotic liver diseases such as liver cirrhosis, diffuse and interlacing bands of fibrous tissue form and replace the normal liver lobules.

Immunology: Enhancement of the immune response through cytokine activation as well as suppression of immunity for prevention of transplant rejection and for treatment of autoimmune disorders may be mediated by altering elastin levels. It has been shown that human activated lymphocytes express the elastin-laminin receptor. The expression of the elastin-laminin receptor is a general property of most activated human lymphocytes, but is dependent upon lymphocyte subsets. Elastin peptides activate these receptors and trigger the stimulation of biosynthesis and release of an elastase.

Ulcerations: Ulcers are defects or excavations of the surface of an organ or tissue, produced by the sloughing of inflammatory tissue. Common ulcerative disorders include esophageal, duodenal, and gastric ulcers. It is believed that providing ulcerative tissues with elastin will speed the healing of the affected tissue and possibly even strengthen the tissue by stimulating endogenous elastin production.

Blood Vessels/Heart: Since large amounts of elastin are found in the walls of blood vessels, particularly in the arch of the aorta near the heart, it is important to maintain the normal healthy balance of elastin in blood vessels and other vessels (such as lymph vessels). Additionally, in pulmonary tissues, the subendothelium is comprised of the internal elastic lamina, a layer which normally separates the endothelium from the underlying smooth muscle cells. In many cardiac diseases such as congestive heart failure, coronary artery disease, homocystinuria, restrictive pericarditis, sclerosing endocarditis, supra ventricular aortic stenosis, this internal elastic lamina is compromised due to the breakdown of elastin resulting in a remodeling of this matrix layer. This breakdown is often the result of an imbalance in enzyme(s) (such as elastase) which degrade elastin. In some cases, such as in Marfan's syndrome, the elastin malformations are due to an autosomal dominant, congenital disorder affecting connective tissue. Thus, providing affected tissue with normal elastin peptides may be a useful treatment for strengthening the connective tissue in individuals with Marfan's syndrome.

A bacterial infection caused by the group A beta hemolytic Streptococci resulting in rheumatic fever can sometimes lead to rheumatic heart disease, a serious condition characterized by inflammation, and degeneration of connective, tissue structures of the body, especially of the heart valves. Treatment of tissues affected by rheumatic heart disease with elastin peptides may allow these tissues to heal and be rebuilt. Additional clinical uses of supplemental elastin peptides include as arterial stents to enhance internal elastic membrane regeneration in angioplasty procedures.

Hypertension: High arterial blood pressure (generally hypertension) can be the result of multiple and diverse etiologies including congenital heart defects, chronic lung disease, hepatic disorders, and autoimmune disease (particularly scleroderma). Hypertension is often marked by endothelial perturbations as well as abnormalities in the subendothelium. These subendothelial problems are manifested in the breakdown of the internal elastic lamina, often by an enzyme which degrades elastin. This breakdown results in the remodeling or rearrangement of the laminar matrix which may result in chronic hypertension. Correcting the elastin composition of the internal elastic lamina with supplemental elastin peptides would improve this condition and would likely augment the standard treatment which includes elastase inhibiting drugs.

With blood vessel and hypertension, a particularly suitable use of the peptides of the present invention would be along with a stent. Depending on the nature of the stent, the stent may have the therapeutic mixture (e.g., peptide(s) alone or in combination with other therapeutic uses) incorporated in the body of the stent or coated thereon. For incorporation, normally a biodegradable plastic stent will be used which will release the therapeutic agents while supporting the vessel and protecting against restenosis. In the fabrication of the stent, the biodegradable matrix may be formed by any convenient means known in the art. Alternatively, the stent may be coated with the therapeutic mixture, using an adhesive or coating which will allow for controlled release of the therapeutic mixture. The stent may be dipped, sprayed or otherwise coated with a composition containing the NO precursor agent or the therapeutic mixture and a matrix, such as biodegradable polymers, a physiologically acceptable adhesive, proteins, polysaccharides or the like. By appropriate choice of the material for the stent and/or the coating comprising the therapeutic mixture, a physiologically active amount of the therapeutic mixture may be maintained at the site of the vascular injury, usually at least one day and up to a week or more.

With the aforementioned wide-spread applicability in mind, a number of peptide or peptide-like compounds were isolated and/or synthesized and analyzed for their suitability as therapeutic, pharmaceutic, or cosmetic agents.

As can be seen from FIG. 1, the topical treatment with a composition which included peptide fragments (i.e., SEQ IDs 1–41) at a concentration of about 1.3% (wt/wt) of the formulation when applied to the skin of a Sprague-Dawley male rat over a one month period illustrates a doubling of the elastin content of the skin, as compared to both control samples and similar applications and concentration of DHEA. In FIG. 1, S CONTR represents the Shaven Control and US CONTR represents the Unshaven Control. FIG. 1 illustrates that the compounds of the present invention have the advantageous qualities of enhancing the softness or elasticity of the skin. The peptides and formulations of the present invention also appear to improve the texture of skin, specifically the physical appearance of the skin.

In the Sprague-Dawley rats used to generate FIG. 1, the rats were treated topically with a 1.3% concentration (wt/wt) of the preparation of the hydrophilic elastin peptide for a period of 30 days. Testing illustrated that the endogenous elastin (measured by microgram ($\mu$g) Elastin per milligram (mg) Skin Fat Free Dry weight) of each of the rats to which the composition was applied doubled over that of a control sample and to a sample which was treated, with a 5% concentration of DHEA over a similar time period. Three animals each were used to generate the data for S CONTR, US CONT, and DHEA and eleven animals were used for HEP. Three skin samples from the treated areas of each animal were taken for study, and the three results from each animal were averaged. The mean of these results were: S CONTR (1.408); US CONTR (2.291); DHEA (1.753); HEP (3.175). The elastin content of the skin was determined by a precise assay for rat elastin developed by Sandberg, et al. (*Connective Tissue Research.* 25: 139–48, 1990) the assay portion of which is hereby incorporated herein by reference thereto. An alpha level less than 0.001 for the data of FIG. 1 as determined by analysis of variance is significant because there is less than one chance in a thousand that the findings occur by chance. The data of FIG. 1 further supports the use of the cosmetic or pharmaceutical preparation over an extended period preferably in the range of one week to one month, more preferably in the range of seven days to about fourteen days and most preferably about, fourteen days of daily administration at about 1.5% concentration (wt/wt) of elastin peptide or peptides with concentrate on pharmaceutical preparation.

FIG. 2 is a micrograph illustrating an increased appearance and beneficial implication of the present invention. From FIG. 2, skin treated with an elastin peptide fragment appears to be healthier than untreated skin. This is evidenced under a microscope by an increase in vascular response. In FIG. 2, fixed tissue sections of rat skin were labeled with fluorescein conjugated antifibronectin antibodies. FIG. 2a is a representative sample from the unshavenicontrol tissue; FIG. 2b is a representative sample from the shaven control sample; and FIG. 2c is a representative sample of the tissue which received DHEA topical treatment. Finally, FIG. 2d received treatment with the present invention a topical form in accordance with the samples discussed above with regard to FIG. 1. The dermal layer in the control panels (FIGS. 2a and 2b) is relatively uniform and thin compared to the thickness of both FIGS. 2c and 2d. For convenience, in each of panels FIGS. 2a–2d, the dermal layer is bracketed. Surprisingly, panel FIG. 2d illustrates an increased concentration of capillary venules in the subdermal region. The capillary venules are shown in this figure as brightly stained oval bodies that lie beneath the dermal layer. The increase in the concentration of endothelial cells in the subdermal region indicates an increase in capillary density and therefore illustrates the potential for the peptides and formulations of the present invention to be used for the formation of blood vessels or capillary venules (neovascularization or angiogenesis).

As can be seen from Table II below, it would appear that certain groups of the peptides described in Table I (inclusive) have preferred characteristics as they relate to cosmetic, pharmaceutical or therapeutic application to the skin. The elastin peptide mixture isolated from thermolysin digestion of elastin (i.e., SEQ ID 1–SEQ ID 41 inclusive) was collected as they came off of a HPLC column. Instead of isolating each of the thermolysin peptide fragments individually, 5 fractions or clusters of peptides were collected in the 5–50 minute range and were tested for activity utilizing a bromodeoxyuridine Triphosphate (BrdUTP) incorporation assay. The assay measures production of mRNA involved in protein synthesis. Table II measures the green fluorescence intensity as a measure of increased mRNA in RFL-6 cells in response to the pooled elastin fragment.

TABLE II

| Fraction # | Approximate Elution time | Approximate % Change w/Control Subtracted Out |
|---|---|---|
| 1 | 5.3 min.–11.8 min | 1% |
| 2 | 11.8 min–23.0 min | 4% |
| 3 | 23.0 min–44.1 min | 41% |
| 4 | 44.1 min–45.8 min | 10% |
| 5 | 45.8 min–50.0 min | 2% |
| 6 | Unfractionalized mixture (SEQ IDs 1–41) | 52% |

Each of the fractions show an increase in mRNA in RFL-6 cells over the control group. From the test, however, it appears that Fraction #3 alone and/or in combination with other fractions (e.g., as seen with Fraction #6) has a preferred composition when increasing elasticity, turgor, and/or appearance of tissue, specifically skin. Fraction 3 includes SEQ IDs 14–31. It should be noted that in light of the ease in obtaining the unfractionalized mixture (as described above) it may be more preferable to use the un fractionalized mixture than isolating the most active ingredient.

Fraction or Cluster 3 was sub-fractionated into 10 fractions corresponding to the ten major peaks identified on the HPLC (at 215 nm). Table III below illustrates the green fluorescence intensity as a measure of increasesd mRNA in RFL-6 cells in response to sub-fractionated portions of Fraction No. 3.

TABLE III

| Fractionated # | Seq. No. Contained Therein | Abbreviated Peptide Sequence | % Change of Green Fluorescence Intensity |
|---|---|---|---|
| 1 | SEQ ID 14 | VGPA | 39 |
| 2 | SEQ IDs 15, 16 | VVPG, AVPG | 40 |
| 3 | SEQ ID 17 | VVPQ | 85 |
| 4 | SEQ IDs 18, 19 | VAARPG, LGAGGAG | 44 |
| 5 | SEQ IDs 20, 21 | AIPG, LGPGG | 42 |
| 6 | SEQ ID 22 | AAAQA | 20 |
| 7 | SEQ ID 23 | VGVHypG | 57 |
| 8 | SEQ ID 24 | VYPGG | 38 |
| 9 | SEQ IDs 25, 26, 27, 28, 29 | IGGVGG, VAPGVG, LGVGG, VLPG, FRAAA | 10 |
| 10 | SEQ IDs. 30, 31 | VGGVPG, FGPGG | 23 |
| Blank (Background) | | | 30 |

As can be clearly seen from Table III, it appears SEQ ID 17 (VVPQ) has the greatest activity, followed by SEQ ID 23 (VGVHypG) and then SEQ IDs 18 (VAARPG) and 19 (LGAGGAG). It would appear that SEQ IDs. 22 and 25–31 actually may adversely impact the overall therapeutic or cosmetic value of Fraction 3. However, applicant does not wish to be bound by this speculation in that any one or combination of these fractions while lowering the green fluorescence intensity of the fractionated sample may in fact add a desirable characteristic to the intended use of the overall mixture or when combined with another peptide (e.g., any of SEQ IDs 1–41 respectively). In other words, other types of testing may in fact demonstrate suitability of other peptide's for pharmaceutical and/or cosmetic purposes, even those adversely indicated herein.

Figure 3:
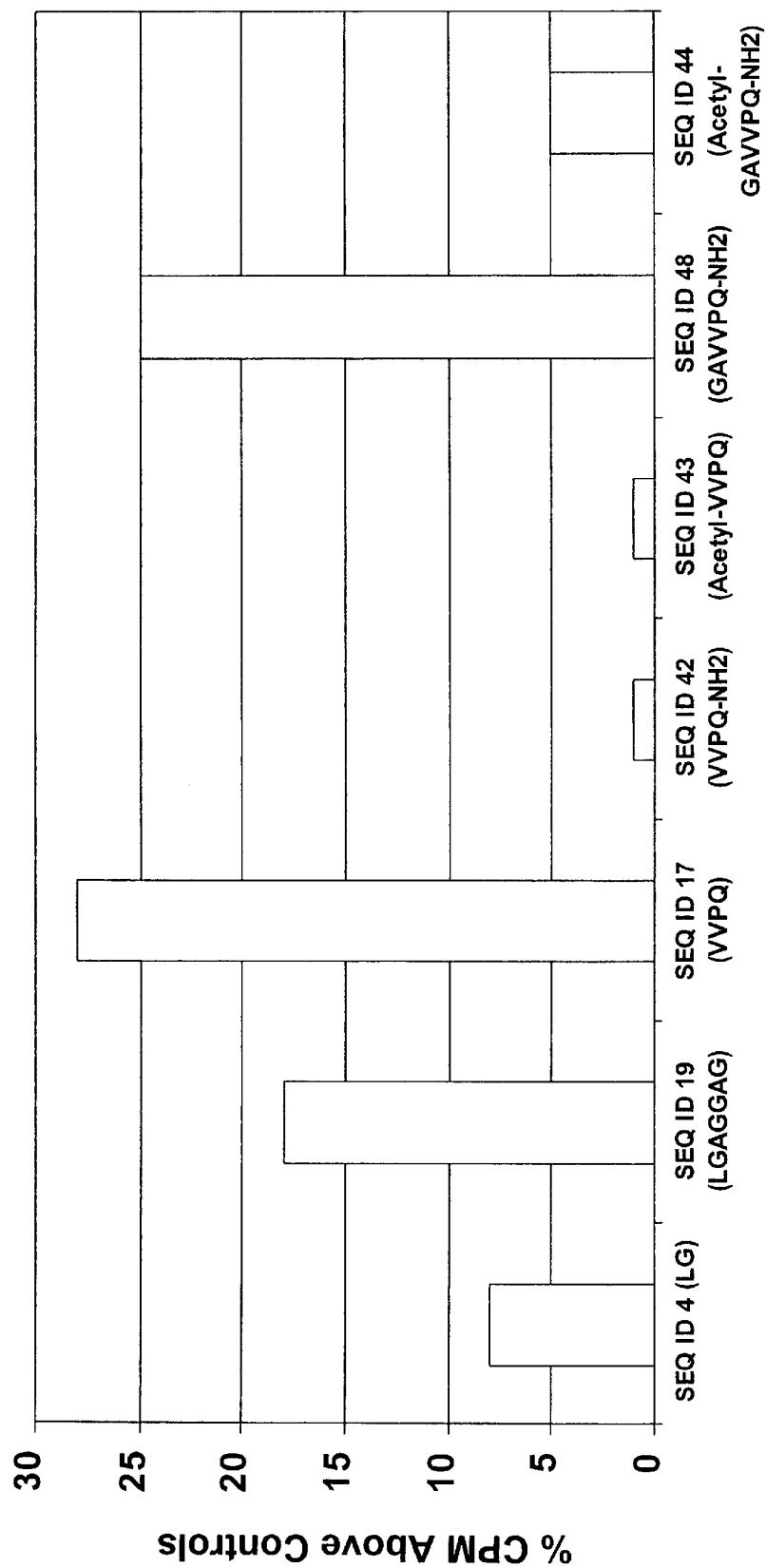
FIG. 3 is a bar graph illustrating tritiated Thymidine incorporation with selected peptide or peptide-like compounds.

The bar graph of FIG. 3 illustrated the potential effect of modifying sequences in a variety of ways. The results of modifying SEQ ID 17 (what appears to be the most active peptide for many purposes) provide important information on the impact of such modifications. For instance, the modifications made to SEQ IDs 42 and 43 appear to adversely impact the suitability for these purposes. SEQ ID 4 (LG) resulted in about an 8% CPM above the control; SEQ ID 17 (VVPQ) resulted in about a 28% CPM above the control; SEQ ID 19 (LGAGGAG) resulted in about an 18% CPM above the control; SEQ ID 42 (VVPQ-NH$_2$) resulted in about a 1% CPM above the control; SEQ ID 43 (Acetyl-VVPQ) resulted in about a 1% CPM above the control; SEQ-ID 48 (GAVVPQ-NH$_2$) resulted in about a 25% CPM above the control; and SEQ ID 44 (Acetyl-GAVVPQ-NH$_2$) resulted in about a 5% CPM above the controls. From FIG. 3 and Table VII it appears that the synthetic peptide SEQ ID 17 appears has the same or nearly the same activity as SEQ ID 17 isolated from the HPLC fractionalization. Accordingly, focus should be placed upon this peptide. It would also appear that a GA residue attached to the N-terminus of the SEQ ID 42 (resulting in SEQ ID 48) has a similar activity to the activity of SEQ ID 17. The ubiquity of the GA residue in an elastin's peptide sequence suggests that such a modification of other peptide fragments may augment their activity and/or otherwise may be desirable. Having an amide at the carboxyl terminus or an acetyl at the N-terminus may also beneficially affect activity and/or solubility of the subject peptide.

The information derived from Table III and FIG. 3 was utilized to systematically synthesize peptides which would appear to be particularly suitable as pharmaceutic, cosmetic, and/or therapeutic compositions. A general method for synthesizing peptides is described in U.S. Pat. No. 4,816,513, incorporated herein by reference thereto in its entirety, which describes a process for automatically constructing a polypeptide. Additionally, U.S. Pat. No. 4,668,476, incorporated herein by reference thereto in its entirety, also describes an apparatus for automatically constructing a polypeptide and a transfer system to transfer activated species from the activator system to the reaction vessel and to transfer amino acids, reagents, gases and solvents from one part of the apparatus to another. Generally, this synthesis process is conducted using Fmoc chemistry on automated solid phase synthesizers, (or in some cases by Boc chemistry). In most cases, the synthesized peptides would be purified by HPLC using reversed phase C4 and C18 columns. Alternate purification methods include ion exchange and gel filtration chromatography.

Our studies indicate that sequences which contain the critical residue VVP have enhanced activity. SEQ ID 17 (VVPQ), for example, showed particularly good activity. Derivatives of SEQ ID 17 were synthesized. Table IV illustrates the three types of derivatives of SEQ ID 17 which were synthesized and determined to be suitable as pharmaceutic, therapeutic, and or cosmetic compositions in accordance with the present invention. SEQ IDs 45–48 illustrate various modifications of VVPQ at either the amino terminus or carboxy terminus of the peptide. SEQ IDs 49–51 have been modified to include a cysteine residue at both the carboxy and amino terminus of the peptides. The cysteine residues provide a sulfhydryl group at each end of the chain which permits convenient formation of cyclic disulfide. Finally, SEQ IDs 52–54 are very similar to SEQ IDs 49–51, but they have copper as a cheating agent to form a cyclic structure.

TABLE IV (VVPQ derived peptides)

| SEQ # | PEPTIDE | MOL WT | NAME (N- to C-terminal) |
|---|---|---|---|
| 42 | VVPQNH$_2$ | 448 | Alanine-Valine-Proline-Glutamine-Amide |
| 43 | (CH$_3$CO)VVPQ | 475 | Acetyl-Valine-Valine-Proline-Glutamine |
| 44 | (CH$_3$CO)GAVVPQNH$_2$ | 610 | Acetyl-Glycine-Alanine-Valine-Valine-Proline-Glutamine-Amide |
| 45 | AVVPQ | 512 | Alanine-Valine-Valine-Proline-Glutamine |
| 46 | GAVVPQ | 569 | Glycine-Alanine-Valine-Valine-Proline-Glutamine |
| 47 | AVVPQNH$_2$ | 519 | Alanine-Valine-Valine-Proline-Glutamine-amide |
| 48 | GAVVPQNH$_2$ | 576 | Glycine-Alanine-Valine-Valine-Proline-Glutamine-amide |
| 49 | CVVPQC (cyclic) | 647 | Cysteine-Valine-Valine-Proline-Glutamine-Cysteine |
| 50 | CAVVPQC (cyclic) | 718 | Cysteine-Alanine-Valine-Valine-Proline-Glutamine-Cysteine |
| 51 | CGAVVPQC (cyclic) | 775 | Cysteine-Glycine-Alanine-Valine-Valine-Proline-Glutamine-Cysteine |
| 52 | Cu-CVVPQC (cyclic) | 64 / 647 | Copper / Cysteine-Valine-Valine-Proline-Glutamine-Cysteine |
| 53 | Cu-CAVVPQC (cyclic) | 64 / 718 | Copper / Cysteine-Alanine-Valine-Valine-Proline-Glutamine-Cysteine |
| 54 | Cu-CGAVVPQC (cyclic) | 64 / 775 | Copper / Cysteine-Glycine-Alanine-Valine-Valine-proline-Glutamine-Cysteine |

Based on the information provided by Table I–Table IV, the VVP sequence appeared important. SEQ ID 55 was synthesized to replace the glutamine of SEQ ID 1:7 with an asparagine (Asp-"N") residue, the glutamine residue and asparagine residue having similar charge properties. Modifications were made to SEQ ID 52 that were very similar to those made to SEQ ID 17. These modified or synthetic peptides are illustrated in Table V.

TABLE V (VVPN derived peptides)

| SEQ # | PEPTIDE | MOL WT | NAME (N- to C-terminal) |
|---|---|---|---|
| 55 | VVPN | 427 | Valine-Valine-Proline-Asparagine |
| 56 | AVVPN | 498 | Alanine-Valine-Valine-Proline-Asparagine |
| 57 | GAVVPN | 555 | Glycine-Alanine-Valine-Valine-Proline-Asparagine |
| 58 | AVVPNNH$_2$ | 505 | Alanine-Valine-Valine-Proline-Asparagine-Amide |
| 59 | GAVVPNNH$_2$ | 562 | Glycine-Alanine-Valine-Valine-Proline-Asparagine-Amide |
| 60 | CVVPNC (cyclic) | 633 | Cysteine-Valine-Valine-Proline-Asparagine-Cysteine |
| 61 | CAVVPNC (cyclic) | 704 | Cysteine-Alanine-Valine-Valine-Proline-Asparagine-Cysteine |
| 62 | CGAVVPNC (cyclic) | 761 | Cysteine-Glycine-Alanine-Valine-Valine-Proline-Asparagine-Cysteine |
| 63 | Cu-CVVPNC (cyclic) | 64 / 633 | Copper / Cysteine-Valine-Valine-Proline-Asparagine-Cysteine |
| 64 | Cu-CAVVPNC (cyclic) | 64 / 704 | Copper / Cysteine-Alanine-Valine-Valine-Proline-Asparagine-Cysteine |

TABLE V-continued

(VVPN derived peptides)

| SEQ # | PEPTIDE | MOL WT | NAME (N- to C-terminal) |
|---|---|---|---|
| 65 | Cu—CGAVVPNC (cyclic) | 64 761 | Copper-Cysteine-Glycine-Alanine-Valine-Valine-Proline-Asparagine-Cysteine |

Since SEQ ID 19 (Leucine-Glycine-Alanine-Glycine-Glycine-Alanine-Glycine) also indicated enhanced activity (see Table III above), it was used as a base model for the synthesis of the peptides shown in Table VI below.

TABLE VI

(LGAGGAG derived peptides)

| SEQ # | PEPTIDE | MOL WT | NAME (N- to C-terminal) |
|---|---|---|---|
| 66 | LGAGGAGV | 600 | Leucine-Glycine-Alanine-Glycine-Glycine-Alanine-Glycine-Valine |
| 67 | LGAGGAGVL | 713 | Leucine-Glycine-Alanine-Glycine-Glycine-Alanine-Glycine-Valine-Leucine |
| 68 | LGAGGAGVNH$_2$ | 607 | Leucine-Glycine-Alanine-Glycine-Glycine-Alanine-Glycine-Valine-Amide |
| 69 | LGAGGAGVLNH$_2$ | 720 | Leucine-Glycine-Alanine-Glycine-Glycine-Alanine-Glycine-Valine-Leucine-Amide |
| 70 | CLGAGGAGC (cyclic) | 707 | Cysteine-Leucine-Glycine-Alanine-Glycine-Glycine-Alanine-Glycine-Cysteine |
| 71 | CLGAGGAGVC (cyclic) | 806 | Cysteine-Leucine-Glycine-Alanine-Glycine-Glycine-Alanine-Glycine-Valine-Cysteine |
| 72 | CLGAGGAGVLC (cyclic) | 919 | Cysteine-Leucine-Glycine-Alanine-Glycine-Glycine-Alanine-Glycine-Valine-Leucine-Cysteine |
| 73 | Cu—CLGAGGAGC (cyclic) | 64 707 | Copper Cysteine-Leucine-Glycine-Alanine-Glycine-Glycine-Alanine-Glycine-Cysteine |
| 74 | Cu—CLGAGGAGVC (cyclic) | 64 806 | Copper Cysteine-Leucine-Glycine-Alanine-Glycine-Glycine-Alanine-Glycine-Valine-Cysteine |
| 75 | Cu—CLGAGGAGVLC (cyclic) | 64 919 | Copper Cysteine-Leucine-Glycine-Alanine-Glycine-Glycine-Alanine-Glycine-Valine-Leucine-Cysteine |

Preliminary data suggests the importance of VVP and VVPQ (e.g. see FIGS. 1–3) as well as LGAGGAG. Further analysis will be conducted to determine the specific suitability of SEQ IDs 1–75 and modification or biological equivalents thereto.

While the foregoing has been set forth in considerable detail, the sequences are presented for elucidation, and not limitation. Modifications and improvements, including equivalents, of the technology disclosed above which are within the purview and abilities. of those in the art are included within the scope of the claims appended hereto. It will be readily apparent to those skilled in the art that numerous modifications, alterations and changes can be made with respect to the specifics of the above description without departing from the inventive concept described herein. For example, the compounds can be administered via many alternative drug delivery vehicles known in the art and the peptides can be derived from digestion of elastin or by amino acid sequencing (either solid state or liquid), as well as from over-expression in a bacterial system. Modification (either chemical or enzymatic) of the basic sequences described herein are also within the purview of the present invention. For example, it appears that a reoccurring pattern in the elastin sequence is the presence of a glycine-alanine residue. Therefore the disclosed sequences may be modified to include this residue at either the amino or carboxyl ends of the peptides. The sequences may also be chemically modified to increase their activity (e.g., amidation of the carboxyl terminus portion of a sequence). The peptides may be chemically modified to increase their activity (e.g., amidation of the carboxy terminus portion of a sequence or including a glycine or alanine residue at either end). Accordingly, all such variances should be viewed as being within the scope of the present invention as set forth in the claims below.

What is claimed is:

1. A composition useful in treating a condition of mammalian tissue, said composition being comprised of a peptide selected from the group consisting of SEQ ID 66, SEQ ID 67, SEQ ID 68, SEQ ID 69, SEQ ID 70, SEQ ID 71, SEQ ID 72, SEQ ID 73, SEQ ID 74, and SEQ ID 75.

2. The composition of claim 1, wherein said peptide is at a therapeutically effective concentration in a range of about 0.0002% to about 90%.

3. The composition of claim 1, wherein said composition is a cosmetic preparation.

4. The composition of claim 3, wherein said cosmetic preparation is formulated as a topical preparation to be applied to a patient's skin.

5. The composition of claim 4, wherein said topical preparation is selected from the group consisting of an emulsion, lotion, spray, aerosol, powder, ointment, cream and foam.

6. The composition of claim 1, wherein the mammalian tissue being treated is a blood vessel.

7. The composition of claim 1, wherein the composition is useful for treating a condition selected from the group consisting of hypertension, coronary heart disease, arteriosclerosis, angina, coronary thrombosis, chronic obstructive pulmonary disease, and restenosis post angioplasty.

8. The composition of claim 1, wherein said peptide is useful in improving tissue turgor.

9. The composition of claim 1, wherein said composition further includes a pharmaceutical delivery system.

10. The composition of claim 9, wherein said pharmaceutical delivery system is selected from the group consisting of a topical delivery system and a subcutaneous delivery system.

11. The composition of claim 10, wherein said topical delivery system is selected from the group consisting of a cosmetic preparation, powder, emulsion, lotion, spray, ointment, aerosol, cream and foam.

12. A peptide having a formula of $R_1$-Leucine-Glycine-Alanine-Glycine-Glycine-Alanine-Glycine-$R_2$, wherein $R_1$ is an amino portion modified to include an amine, amide, or amino acid sequence having 1–10 amino acids and $R_2$ is a carboxy portion modified to include an amide, ester, or carboxy terminus sequence having 1–10 amino acids.

13. A method of enhancing tissue elasticity, comprising administering a therapeutically effective concentration of a peptide selected from the group consisting of SEQ ID 66, SEQ ID 67, SEQ ID 68, SEQ ID 69, SEQ ID 70, SEQ ID 71, SEQ ID 72, SEQ ID 73, SEQ ID 74, and SEQ ID 75.

14. The method of claim 13, wherein the tissue is selected from the group consisting of a blood vessel, lung tissue, and skin.

15. The method of claim 13, wherein the step of administering the peptide is repeated over a predetermined time period.

16. The method of claim 13, wherein the peptide is an active ingredient in a cosmetic formulation.

* * * * *

UNITED STATES PATENT AND TRADEMARK OFFICE
CERTIFICATE OF CORRECTION

PATENT NO. : 6,506,731 B1
DATED : January 14, 2003
INVENTOR(S) : Lawrence B. Sandberg et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154(b) by 0 days --.

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,506,731 B1
DATED : January 14, 2003
INVENTOR(S) : Lawrence B. Sandberg et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154(b) by 45 days. --.

Signed and Sealed this

Twenty-eighth Day of February, 2006

JON W. DUDAS
*Director of the United States Patent and Trademark Office*